(12) United States Patent
Herzig et al.

(10) Patent No.: US 7,126,020 B2
(45) Date of Patent: Oct. 24, 2006

(54) PROCESS FOR PREPARING HIGHLY VISCOUS ORGANOPOLYSILOXANES

(75) Inventors: Christian Herzig, Waging (DE); Siegfried Dormeier, Stubenberg (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 11/007,387

(22) Filed: Dec. 8, 2004

(65) Prior Publication Data
US 2005/0131243 A1    Jun. 16, 2005

(30) Foreign Application Priority Data
Dec. 11, 2003    (DE) ................ 103 58 060

(51) Int. Cl.
*C07F 7/04* (2006.01)
(52) U.S. Cl. .................. 556/413; 556/450
(58) Field of Classification Search ........... 556/413, 556/450
See application file for complete search history.

(56) References Cited

U.S. PATENT DOCUMENTS

| | | | |
|---|---|---|---|
| 3,658,864 A | 4/1972 | Golitz et al. | |
| 5,241,034 A | 8/1993 | Herzig et al. | |
| 6,252,100 B1 | 6/2001 | Herzig | |
| 6,451,909 B1 | 9/2002 | Herzig et al. | |

FOREIGN PATENT DOCUMENTS

| | | |
|---|---|---|
| DE | 1 905 101 | 8/1970 |
| DE | 25 00 020 | 7/1976 |
| EP | 0 874 017 A2 | 10/1998 |

OTHER PUBLICATIONS

English Derwent Abstract AN 1976-56153X[30] corresponding to DE 25 000 20 A1.

*Primary Examiner*—Samuel Barts
(74) *Attorney, Agent, or Firm*—Brooks Kushman P.C.

(57) ABSTRACT

Process for preparing highly viscous organopolysiloxanes by reacting siloxanes (1) composed of units of the general formula $$A_a R_c (OR^1)_d SiO_{\frac{4-(a+c+d)}{2}} \quad (I)$$

where
A is a nitrogen-containing Si—C-bonded radical,
R is a $C_{1-18}$ hydrocarbon radical
$R^1$ is hydrogen or a $C_{1-8}$ alkyl radical,
a and d are 0 or 1, c is 0, 1, 2 or 3,
a+c+d is <3 and one A and one $R^1$ where of $R^1$ is hydrogen atom are present,
optionally siloxanes (2)

$$R_c(OR^1)_d SiO_{\frac{4-(c+d)}{2}} \quad (II)$$

where
c+d is ≦3 and one $R^1$ radical is hydrogen is present,
with silanes (3)

$$BR_e Si(OR^3)_{3-e} \quad (III)$$

where
B is a radical —$CR^2_2$—Y,
$R^2$ is hydrogen or $C_{1-4}$ alkyl,
Y is halogen, a monosubstituted O and S atom, or a substituted N or P atom,
$R^3$ is $C_{1-8}$ alkyl, and
e is 0, 1 or 2.

11 Claims, No Drawings

PROCESS FOR PREPARING HIGHLY VISCOUS ORGANOPOLYSILOXANES

BACKGROUND OF THE INVENTION

1. Field of the Invention

The invention relates to a process for preparing highly viscous organopolysiloxanes, and to highly viscous organopolysiloxanes prepared thereby.

2. Background Art

For the preparation of polysiloxanes having high viscosity, a number of methods exist, based predominately on condensation reactions. For instance, a standard method is to prepare silanol-functional, highly viscous polysiloxanes from low-viscosity hydrolyzates of chlorosilanes, usually dimethyldichlorosilane, by condensing them at relatively high temperature, usually under the action of acidic catalysts, and liberating water in the process.

In a similar manner, silanol-functional polysiloxanes can be condensed with methoxysilanes to liberate methanol. For this purpose, catalysts and relatively high temperatures are usually required in order to achieve industrially acceptable conversion rates. For instance, the standard process for preparing typical commercial amino-functional siloxanes is the base-catalyzed condensation of aminoalkyl methoxysilanes with a short-chain hydrolyzate of dimethyldichlorosilane at elevated temperature.

In view of the reaction temperatures of 100° C. and higher, and a reaction time of over several hours, a process for preparing highly viscous polysiloxanes is desirable which is either rapidly complete or proceeds at low temperature such as room temperature, or both.

DE-A 2500020 describes a process for preparing aminosiloxanes in which silanol-terminated polysiloxanes are reacted with a-aminosilanes which bear an alkoxy group. The reaction proceeds at moderate temperatures with elimination of alcohol. However, it is only possible with this technique to prepare comparatively unstable α-aminosiloxanes and also only in difunctional telechelic form.

Highly viscous polysiloxanes can also be obtained by polyaddition reactions, as described in U.S. Pat. Nos. 5,241,034 and 6,252,100. EP-A 874 017 and U.S. Pat. No. 6,451,909 disclose polyaddition reactions in emulsion for the preparation of highly viscous polysiloxanes. However, it is common to all of these polyaddition methods that metal catalysts are required for the progress of the reaction, and these are often undesired. In the presence of N-containing sil(ox)anes, catalyst inhibition also occurs, so that it is barely possible, if at all, to carry out an efficiently catalyzed polyaddition.

SUMMARY OF THE INVENTION

It is therefore an object of the invention to provide a process for preparing highly viscous organopolysiloxanes which contain Si—C-bonded radicals containing basic nitrogen, in which the aforementioned disadvantages are avoided and the organopolysiloxanes can be prepared under moderate thermal conditions. It is a further object of the invention to provide highly viscous organopolysiloxanes which contain Si—C-bonded radicals containing basic nitrogen, which are stable. These and other objects are achieved by the invention.

DETAILED DESCRIPTION OF THE PREFERRED EMBODIMENTS

The invention provides a process for preparing highly viscous organopolysiloxanes, which comprises reacting siloxanes (1) composed of units of the general formula

$$A_a R_c (OR^1)_d SiO_{\frac{4-(a+c+d)}{2}} \quad (I)$$

where

A is a monovalent, Si—C-bonded radical having basic nitrogen,

R is a monovalent, optionally substituted hydrocarbon radical having from 1 to 18 carbon atoms per radical, $R^1$ is a hydrogen atom or an alkyl 8 carbon atoms, preferably a hydrogen atom or a methyl or ethyl radical, a is 0 or 1, c is 0, 1, 2 or 3 and d is 0 or 1, with the proviso that the sum of a+c+d is $\leq 3$ and that, on average, at least one A radical and at least one $R^1$ which is a hydrogen atom, are present per molecule, and optionally siloxanes (2) composed of units of the general formula

$$R_c (OR^1)_d SiO_{\frac{4-(c+d)}{2}} \quad (II)$$

where R, $R^1$, c and d are each as defined above, with the proviso that the sum of c+d is $\leq 3$, and at least one $R^1$ radical is a hydrogen atom, with silanes (3) of the general formula

$$BR_e Si(OR^3)_{3-e} \quad (III)$$

where

B is a monovalent radical of the formula —$CR^2_2$—Y, $R^2$ is a hydrogen atom or an alkyl radical having from 1 to 4 carbon atoms, preferably a hydrogen atom, Y is a monofunctional radical from among the halogens, monosubstituted O and S atoms, and substituted N and P atoms, $R^3$ is an alkyl radical having from 1 to 8 carbon atoms per radical, and e is 0, 1 or 2, preferably 0 or 1.

The invention further provides highly viscous organopolysiloxanes composed of units of the general formula

$$A_a B_b R_c (OR^1)_d SiO_{\frac{4-(a+b+c+d)}{2}} \quad (IV)$$

where A, B, R, $R^1$, a, c and d are each as defined above, and b is 0 or 1, with the provisos that the sum of a+b+c+d is $\leq 3$, a and b in the same siloxane unit are not simultaneously 1, and that on average, at least one A radical and one B radical are present per molecule.

The highly viscous organopolysiloxanes obtained by the inventive process are more stable than the organopolysiloxanes obtained by the process described in DE 25 00 020 A, which are unstable since the amino groups are readily eliminated thermally and/or in the acidic pH range, observable as a decrease in the amine number (ml of 1N HCl required to neutralize 1 g of substance.).

Examples of R radicals are alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals, hexyl radicals such as the n-hexyl radical, heptyl radicals such as the n-heptyl radical, octyl radicals such as the n-octyl radical and isooctyl radicals such as the 2,2,4-trimethylpentyl radical, nonyl radicals such as the n-nonyl radical, decyl radicals such as the n-decyl radical, dodecyl radicals such as the n-dodecyl radical, and octadecyl radicals such as the n-octadecyl radical; cycloalkyl radicals such as the cyclopentyl, cyclohexyl, cycloheptyl and methylcyclohexyl radicals; alkenyl radicals such as the vinyl, 5-hexenyl, cyclohexenyl, 1-propenyl, allyl, 3-butenyl and 4-pentenyl radicals; alkynyl radicals such as the ethynyl, propargyl and 1-propynyl radicals; aryl radicals such as the phenyl, naphthyl, anthryl and phenanthryl radicals; alkaryl radicals such as the o-, m-, p-tolyl radicals, xylyl radicals and ethylphenyl radicals; and aralkyl radicals such as the benzyl radical, and the α- and the β-phenylethyl radicals.

Examples of substituted R radicals are haloalkyl radicals such as the 3,3,3-trifluoro-n-propyl radical, the 2,2,2,2',2', 2'-hexafluoroisopropyl radical, the hexafluoroisopropyl radical and haloaryl radicals such as the o-, m- and p-chlorophenyl radicals.

Examples of alkyl radicals $R^1$ are the methyl, ethyl, n-propyl, isopropyl, 1-n-butyl, 2-n-butyl, isobutyl, tert-butyl, n-pentyl, isopentyl, neopentyl, and tert-pentyl radicals, hexyl radicals such as the n-hexyl radical, heptyl radicals such as the n-heptyl radical, octyl radicals such as the n-octyl radical and isooctyl radicals such as the 2,2,4-trimethyl pentyl radical.

Examples of alkyl radicals $R^2$ are the methyl, ethyl, n-propyl, isopropyl, 1-n-butyl, 2-n-butyl, isobutyl and tert-butyl radicals.

Examples of alkyl radicals $R^1$ are fully applicable to alkyl radicals $R^3$.

The A radical is preferably a radical of the formula

$$R^5_2N-(CHR^2)_n-$$  (V)

where $R^2$ is as defined above and is preferably a hydrogen atom, $R^5$ is the same or different and is a hydrogen atom or an alkyl, cycloalkyl or aminoalkyl radical and n is an integer from 2 to 10, preferably from 2 to 4, preferentially 3.

Examples of $R^5$ radicals include the alkyl radicals and cycloalkyl radicals recited for the R radical, and also aminoalkyl radicals, preference among the aminoalkyl radicals given to the aminoethyl radical.

Examples of A radicals are 3-aminopropyl, 3-methylaminopropyl, 3-dimethylaminopropyl, 3-diethylaminopropyl, 3-cyclohexylaminopropyl, 3-(2-aminoethyl)aminopropyl, 3-(3-aminopropyl)aminopropyl, 3-(3-dimethylaminopropyl) aminopropyl, 3,3-bis(dimethylaminopropyl)aminopropyl, and also semiacylated forms from reaction with carboxylic acids such as acetic acid, and semiamidated forms from reaction with lactones such as butyrolactone or valerolactone.

Examples of Y radicals are fluorine, chlorine, bromine, and iodine, —OH and —OR$^4$ groups, the —SH and —SR$^4$ groups, —NH$_2$, —NHR$^4$ and —NR$^4_2$ groups, and the —PR$^4_2$, —P(OR$^4$)$_2$, and —PO(OR$^4$)$_2$ groups, where R$^4$ is a monovalent organic radical optionally containing nitrogen and/or oxygen atoms, preferably a monovalent hydrocarbon radical optionally containing nitrogen and/or oxygen atoms and having from 1 to 18 carbon atoms, Examples of B radicals are hydroxymethyl, methoxymethyl, ethoxymethyl, 2-ethoxyethoxymethyl, 2-butoxyethoxymethyl, acetoxymethyl, mercaptomethyl, ethylthiomethyl, dodecylthiomethyl, aminomethyl, methylaminomethyl, dimethylaminomethyl, diethylaminomethyl, dibutylaminomethyl, cyclohexylaminomethyl, anilinomethyl, 3-dimethylaminopropylaminomethyl, bis(3-dimethylaminopropyl)aminomethyl, diethylphosphinomethyl, dibutylphosphinomethyl, and groups of the formulae —CH$_2$NHCOR$^4$, —CH$_2$NHCO$_2$R$^4$ or —CH$_2$NHCONHR$^4$, where R$^4$ is as defined above. B is preferably a radical of the formula —CH$_2$NHR$^4$ or —CH$_2$NR$^4_2$, where R$^4$ is as defined above.

Examples of hydrocarbon radicals R are applicable fully to hydrocarbon radicals R$^4$.

Preferred siloxanes (1) are those of the general formula

$$(R^1O)R_2SiO(SiR_2O)_n(SiRAO)_mSiR_2(OR^1)$$ (VI)

where A, R and $R^1$ are each as defined above,
m is an integer from 1 to 30, and
n is 0 or an integer from 1 to 1000.

When siloxanes (2) are also used, preference is given to using those of the general formula

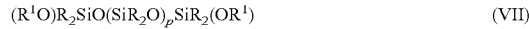

$$(R^1O)R_2SiO(SiR_2O)_pSiR_2(OR^1)$$ (VII)

where R and $R^1$ are each as defined above and
p is an integer from 1 to 1000.

Examples of siloxanes (1) are commercial amine oils having, for example, 3-(2-aminoethyl)aminopropyl groups and which also contain silanol groups, while examples of siloxanes (2) which are optionally employed, include commercial polydimethylsiloxanes having terminal silanol groups. These compounds are obtainable very inexpensively, which makes the process according to the invention particularly attractive economically.

When siloxanes (2) are also used in the inventive process, preference is given to using them in amounts of from 0.01 to 10 kg, preferably from 0.1 to 5 kg, based in each case on 1 kg of siloxane (1).

Examples of silanes (3) are 2-butoxyethoxymethyltrimethoxysilane, methoxymethylmethyldiethoxysilane, diethylaminomethylmethyldimethoxysilane, dibutylaminomethyltriethoxysilane, dibutylaminomethyltributoxysilane, cyclohexylaminomethyltrimethoxysilane, cyclohexylaminomethyltriethoxysilane, cyclohexylaminomethylmethyldiethoxysilane, anilinomethyltriethoxysilane, 3-dimethylaminopropylaminomethyltrimethoxysilane, acetylaminomethylmethyldimethoxysilane and ethylcarbamoylmethyltrimethoxysilane.

In the process of the invention, silanes (3) are preferably used in amounts of from 0.01 to 10% by weight, preferentially from 0.1 to 2.0% by weight, based in each case on siloxane (1) and any siloxane (2) also used.

The process is preferably carried out at temperatures below 100° C., preferentially at from 10 to 70° C., more preferably at from 15 to 40° C. In addition, the process is preferably carried out at the pressure of the surrounding atmosphere, but may also be carried out at higher or lower pressures.

The highly viscous organopolysiloxanes preferably have viscosities of from 1000 mPa·s to 50,000,000 mPa·s at 25° C., more preferably from 10,000 mPa·s to 10,000,000 mPa·s at 25° C. and most preferably from 50,000 mPa·s to 5,000,000 mPa·s at 25° C.

The products may be prepared in bulk, i.e. neat, but it is recommended for handling reasons to dilute with organic solvents or low-viscosity oligomers/polymers during preparation, preferably with siloxanes such as dimethylpolysiloxanes. Examples of organic solvents are toluene, n-hexane, n-heptane, technical benzine fractions, acetone, isopropanol, and ethanol.

Depending on the nature of di- or trialkoxysilane (3) and the linear or branched siloxane(s) (1) and optionally (2), the highly viscous organopolysiloxanes may likewise have linear, branched or even highly branched structures.

In the normal case, the reaction of (1) and, where appropriate (2), with (3), proceeds to completion without addition of catalysts in from a few minutes up to several hours. Methoxysilanes react more rapidly than ethoxysilanes. However, the condensation may be accelerated by acids and bases, and also by compounds of aluminum, magnesium, titanium, zirconium, bismuth, zinc or tin, if desired.

Examples of catalysts (4) which are optionally employed are butyl titanates and organic tin compounds such as di-n-butyltin diacetate, di-n-butyltin dilaurate, dioctyltin dilaurate, di-n-butyltin oxide and tin octoate.

The alcohols obtained as condensation by-products in the process may remain in the product or else be removed, for example by distillation under reduced pressure or by extraction.

In the examples, the following reactants are used:

Amine Oil A:

Copolymer of aminoethylaminopropylmethylsiloxy and dimethylsiloxy units having a content of terminal OH groups of 630 ppm by weight and a viscosity of 4200 mm$^2$/s at 25° C. The amine number is 0.14.

Amine Oil B:

Copolymer of aminoethylaminopropylmethylsiloxy and dimethylsiloxy units having a content of terminal OH groups of 280 ppm by weight and a viscosity of 1100 mm$^2$/s at 25° C. The amine number is 0.30.

PDMS A:

Polydimethylsiloxanediol having a content of terminal OH groups of 1130 ppm by weight.

PDMS B:

Polydimethylsiloxanediol having a content of terminal OH groups of 770 ppm by weight.

EXAMPLE 1

200 g of amine oil A (7.4 meq. of SiOH) are mixed intensively at 25° C. with 0.50 g of aminomethylmethyldimethoxysilane (7.4 meq. of SiOMe). Within 8 hours, a clear viscous oil having a viscosity of 105 Pa·s (25° C.) is formed. The methanol content is 0.118%.

EXAMPLE 2

The method of example 1 is repeated with the modification that, instead of the difunctional aminomethylmethyldimethoxysilane, 0.37 g of the trifunctional aminomethyltrimethoxysilane (7.4 meq. of SiOMe) is used. After 8 hours, an extremely pseudoplastic clear oil having more than 5000 Pa·s (25° C.) is obtained. After heat treatment at 70° C./24 h, the oil is unchanged and is readily soluble in toluene to give a clear solution. The solution is free of gel fractions.

EXAMPLE 3

Example 2 is repeated with half the amount (0.19 g) of aminomethyltrimethoxysilane. After 8 hours, a very pseudoplastic clear oil having a viscosity of approx. 900 Pa·s (25° C.) is obtained. The product is soluble in toluene to give a clear solution and free of gel fractions.

EXAMPLE 4

100 g of amine oil A (3.7 meq. of SiOH) are mixed intensively at 25° C. with 0.41 g of diethylaminomethylmethyldiethoxysilane (3.7 meq. of SiOEt). The increase in viscosity which sets in slowly attains a value of 50 Pa·s (25° C.) after 24 hours.

EXAMPLE 5

100 g of amine oil A (3.7 meq. of SiOH) are mixed homogeneously at 25° C. with 0.34 g of cyclohexylaminomethyltriethoxysilane. After only a few minutes, the viscosity rises considerably. After 24 hours, a clear, solid mass is obtained which is fully soluble in toluene.

EXAMPLE 6

100 g of amine oil A (3.7 meq. of SiOH) are mixed homogeneously at 25° C. with only 0.25 g of cyclohexylaminomethyltriethoxysilane. Even with a smaller amount of reactive silane, a rapid viscosity rise is visible, but only 120 Pa·s (25° C.) are attained after 24 hours.

EXAMPLE 7

100 g of amine oil B (1.65 meq. of SiOH) are homogenized with 45 g of PDMS A (3.0 meq. of SiOH) and then mixed with 0.60 g of cyclohexylaminomethylmethyldiethoxysilane (4.65 meq. of SiOEt). After 8 hours, a rapid viscosity rise leads to a product having 52 Pa·s (25° C.).

EXAMPLE 8

55 g of amine oil A are homogenized with 45 g of PDMS B (in each case 2.04 meq. of SiOH). In addition, 0.53 g of cyclohexylaminomethylmethyldiethoxysilane (4.08 meq. of SiOEt) is mixed in. After 24 hours, the clear homogeneous oil has a viscosity of 1050 Pa·s (25° C.).

EXAMPLE 9

Example 8 is repeated with the modification that both siloxanes, amine oil A and PDMS B, before the silane is added, are diluted with 100 g of silicone oil of viscosity 35 mPa·s (25° C.). After 24 hours, the 50% amine oil solution attains a viscosity of 20,000 mPa·s (25° C.).

EXAMPLE 10

The product, prepared in example 7, having a viscosity of 52 Pa·s (25° C.) has an amine number of 0.321 (equivalent of basic nitrogen titratable with HCl). 50 g thereof are mixed with 0.96 g of glacial acetic acid and heat-treated at 70° C. for 24 h. Afterward, the amine number is measured again. Its value is then 0.312. At 97.2% of the starting value, the amine number is virtually unchanged.

Comparative Experiment:

According to DE 2500020 A, 304.3 g of a siloxanediol of the average formula $HO(Me_2SiO)_{82}H$ and 11.9 g of aminomethyldimethylmethoxysilane are used to prepare 316.2 g of an α,ω-bis(aminomethyl)polydimethylsiloxane which has an amine number of 0.314. After homogeneously mixing in 0.97 g of glacial acetic acid and heat-treating at 70° C. over 24 h, a value of only 0.014 is measured. This corresponds to only 4.5% of the original value. In the $^1H$ NMR spectrum, only traces of the aminomethyl group can still be detected.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for preparing viscous organopolysiloxanes, which comprises reacting siloxanes (1) comprising units of the formula $$A_a R_c (OR^1)_d SiO_{\frac{4-(a+c+d)}{2}} \quad (I)$$

where
- A is a monovalent, Si—C-bonded radical containing basic nitrogen,
- R is a monovalent, optionally substituted hydrocarbon radical having from 1 to 18 carbon atoms per radical,
- $R^1$ is a hydrogen atom or an alkyl radical having from 1 to 8 carbon atoms,
- a is 0 or 1,
- c is 0, 1, 2 or 3, and
- d is 0 or 1, with the provisos that the sum of a+c+d is ≦3, on average at least one A radical, and at least one $R^1$ radical in which $R^1$ is a hydrogen atom are present per molecule, and optionally siloxanes (2) comprising of units of the formula $$R_c (OR^1)_d SiO_{\frac{4-(c+d)}{2}}, \quad (II)$$

with the provisos that the sum of c+d is ≦3 and at least one $R^1$ radical is a hydrogen atom, with silanes (3) of the formula $$BR_e Si(OR^3)_{3-e} \quad (III)$$

where
- B is a monovalent radical of the formula —$CR^2_2$—Y,
- $R^2$ is a hydrogen atom or an alkyl radical having from 1 to 4 carbon atoms,
- Y is a monofunctional radical selected from the group consisting of the halogens, monosubstituted O and S atoms, and substituted N and P atoms,
- $R^3$ is an alkyl radical having from 1 to 8 carbon atoms per radical, and
- e is 0, 1 or 2.

2. The process of claim 1, wherein $R^1$ is a radical selected from the group consisting of hydrogen, methyl, and ethyl.

3. The process of claim 1, wherein $R^2$ is hydrogen.

4. The process of claim 1, wherein e is 0 or 1.

5. The process of claim 1, wherein the A radical is a radical of the formula $$R^5_2N—(CHR^2)— \quad (V)$$

where $R^5$ is the same or different and is a hydrogen atom or an alkyl, cycloalkyl or aminoalkyl radical, and
n is an integer from 2 to 10.

6. The process of claim 5, wherein $R^2$ is hydrogen.

7. The process of claim 1, wherein the A radical is a 3-(2-aminoethyl)aminopropyl radical.

8. The process of claim 1, wherein the A radical is a 3-aminopropyl radical.

9. The process of claim 1, wherein the B radical is a radical of the formula —$CH_2NHR^4$ or —$CH_2NR^4_2$, where R4 is a monovalent hydrocarbon radical optionally containing nitrogen and/or oxygen atoms and having from 1 to 18 carbon atoms.

10. The process of claim 1, wherein at least one siloxane (1) is one of the formula $$(R^1O)R_2SiO(SiR_2O)_n(SiRAO)_m SiR_2(OR^1) \quad (VI)$$

where m is an integer from 1 to 30, and
n is 0 or an integer from 1 to 1000.

11. The process of claim 1, wherein at least one siloxane (2) is one of the formula $$(R^1O)R_2SiO(SiR_2O)_p SiR_2(OR^1) \quad (VII)$$

where p is an integer from 1 to 1000.

* * * * *

UNITED STATES PATENT AND TRADEMARK OFFICE
CERTIFICATE OF CORRECTION

PATENT NO.       : 7,126,020 B2                                    Page 1 of 1
APPLICATION NO.  : 11/007387
DATED            : October 24, 2006
INVENTOR(S)      : Christian Herzig et al.

It is certified that error appears in the above-identified patent and that said Letters Patent is hereby corrected as shown below:

Column 8, Line 34, Claim 9

Delete "R4" and insert therefor -- $R^4$ --.

Signed and Sealed this

Sixteenth Day of January, 2007

JON W. DUDAS
*Director of the United States Patent and Trademark Office*